United States Patent [19]

Kaluza et al.

[11] Patent Number: 5,134,067

[45] Date of Patent: Jul. 28, 1992

[54] TYPE II RESTRICTION ENDONUCLEASE RLEAI

[75] Inventors: Klaus Kaluza; Michael Jarsch, both of Bad Heilbrunn; Gudrun Schmitz-Agheguian, Bernried; Christoph Kessler, Dorfen, all of Fed. Rep. of Germany

[73] Assignee: Boehringer Mannheim GmbH, Mannheim, Fed. Rep. of Germany

[21] Appl. No.: 616,623

[22] Filed: Nov. 16, 1990

[30] Foreign Application Priority Data

Nov. 16, 1989 [DE] Fed. Rep. of Germany ....... 3938145
Mar. 7, 1990 [DE] Fed. Rep. of Germany ....... 4007043

[51] Int. Cl.$^5$ ................... C12P 19/34; C12N 9/22
[52] U.S. Cl. .................... 435/91; 435/199; 435/878
[58] Field of Search ............ 435/199, 91, 878

[56] References Cited

PUBLICATIONS

Vesely, Z. et al. (1990) Gene 95, 129-131.

*Primary Examiner*—Charles L. Patterson, Jr.
*Attorney, Agent, or Firm*—Felfe & Lynch

[57] ABSTRACT

The type II restriction endonuclease RleAI has the following recognition sequence:

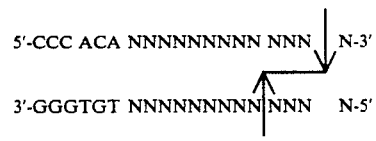

cleaves DNA at the cleavage site indicated by the arrows, and is preferably obtainable from microorganisms of the genus Rhizobium. It can be used to recognize and cleave the double-stranded DNA sequence CCCA-CA(N)$_{12/9}$ and its complementary sequence.

10 Claims, No Drawings

TYPE II RESTRICTION ENDONUCLEASE RLEAI

FIELD OF THE INVENTION

The invention concerns the type II restriction endonuclease RleAI, a process for its isolation and its use.

BACKGROUND AND PRIOR ART

Type II restriction endonucleases are endodeoxyribonucleases which are able to recognize and cleave particular DNA sequences. In this process one phosphodiester bridge is hydrolyzed in each polynucleotide strand of the target sequence. Type II restriction endonucleases are thus of value for the analysis of DNA molecules. Although type II restriction endonucleases are known which are specific for numerous DNA sequences, there is still a need for further restriction endonucleases with new specificities.

SUMMARY OF THE INVENTION

The present invention is a type II restriction endonuclease having the recognition sequence

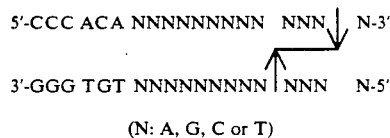

(N: A, G, C or T)

and the cleavage site defined by the arrows.

DETAILED DESCRIPTION OF PREFERRED EMBODIMENTS

The new restriction endonuclease according to the present invention, which is denoted RleAI hereafter, has a temperature optimum at ca. 30° C. The enzyme has good activity between pH 7.5 and pH 8.0 in 10 mmol/l Tris/HCl, 10 mmol/l $MgCl_2$ and 1.0 mmol/l DTE (dithioerythritol). The pH optimum is at ca. pH 7.5. An enzyme which has the same recognition sequence and cleavage site as RleAI is not known.

The recognition sequence can be confirmed by the complete digestion of DNA of the SV40 and adeno 2 viruses, of phage lambda and phage phiX174 and of the phage derivative M13mp8. These DNA molecules are treated with RleAI.

Table 1 shows a comparison of the cleavage site specificity observed with a cleavage site specificity determined by a computer for an enzyme which recognizes the sequence $CCCACA(N)_{12/9}$.

The cleavage position within the recognition sequence of the enzyme can be dermined on a M13 derivative having this recognition sequence at an interval of ca. 30-200 bases from the binding site of the universal sequencing primer (Messing, J. et al., (1981) Nucl. Acids Res. 9, 309-321). At first sequencing reactions according to the dideoxy chain-termination method (Sanger, F. et al., (1977) Proc. Natl. Acad. Sci. USA 74 560-564, Messing, J. et al., (1981) Nucl. Acids Res. 9, 309-321) are carried out on the single-stranded DNA of the M13 derivative with the universal sequencing primer.

Parallel with this, the sequencing primer is radioactively labelled at the 5' end with T4-polynucleotide kinase and $[\gamma-^{32}p]ATP$. After hybridization of this 5' end-labelled sequencing primer to the single-stranded M13 DNA, a partially double-stranded DNA is prepared in a "filling in" reaction with DNA-polymerase I (Klenow enzyme) and a deoxynucleotide triphosphate mixture of dATP, dCTP, dGTP and dTTP. An aliquot of this DNA, of which the newly synthesized strand is radioactively labelled at the 5' end is now cleaved with the restriction endonuclease RleAI. Half of the cleavage preparation is additionally treated with T4-DNA polymerase in the presence of a mixture of all four deoxynucleotide triphosphates in order to obtain blunt DNA ends.

The analysis of the reaction products is carried out by electrophoresis on sequencing gels (8 mol/l urea, 5% polyacrylamide) and subsequent autoradiography.

The results are interpreted according to Brown, N. L. and Smith, M. (Methods in Enzymology 65 (1980) 391-401). The position of the cleavage site is determined by a comparison of the distances of migration of the radioactively-labelled fragments with the sequencing ladder. The samples which were additionally treated with T4-DNA polymerase show a band which is three base pairs shorter in comparison with the samples which were only cleaved with RleAI. This therefore shows that RleAI produces a 3' end which protrudes by 3 base pairs.

RleAI has therefore the following cleavage specificity inside of the recognition sequence:

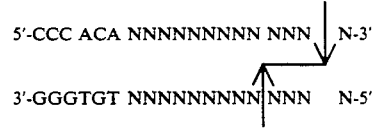

The number of cleavage sites determined experimentally is identical to the number of cleavage sites for the recognition sequence $CCCACA(N)_{12/9}$ obtained by computer analysis with the different DNA's (Table I). In addition these data were also compared with the tables in Gene 10 (1980) 357-370. A double digestion of SV 40 DNA by BamHI und RleAI confirms that the recognition sequence is $CCCACA(N)_{12/9}$.

RleAI is preferably isolated by culturing microorganisms of the genus *Rhizobium*, preferably microorgan-

TABLE 1

| DNA | Fragment lengths determined experimentally [bp] | Fragment lengths determined by computer analysis [bp] | Cleavage positions determined by computer analysis at the base pairs | Number of cleavage sites determined by computer analysis | Number of cleavage sites determined experimentally |
|---|---|---|---|---|---|
| SV 40 | 2250, 1300 790, 470, 400 | 2296, 1272, 793, 473, 409 | 1825, 2298 2707, 3500 4772 | 5 | 5 |
| M13mp8 | 7200 | 7229 | 3009 | 1 | 1 |
| phiX174 | 5400 | 5386 | 576 | 1 | 1 | bp: base pair(s)

isms of the species *Rhizobium lequminosarum* and isolating the enzyme from the cells. In particular DSM 5629 is preferred.

The microorganism *Rhizobium leguminosarum* was deposited at the German Collection for Microorganisms, Gesellschaft für biotechnologische Forschung mbH, Mascheroder Weg 1b, 3300 Braunschweig, BRD and has the deposit number DSM 5629.

The microorganisms used for the isolation of the enzyme grow aerobically in a PSY medium which includes the following components:

0,3 g/l $KH_2PO_4$
0.3 g/l $Na_2HPO_4$
0.1 g/l $MgSO_4 \cdot 7H_2O$
0.07 g/l $CaCl_2 \cdot 2H_2O$
3 g/l Pepton
1g/l yeast extract
2 ml/l trace elements 500 x (*)
1 ml/l vitamins 1000 x (**)
(*)—trace elements 500 x:
5 g/l $H_3BO_3$
500 mg/l $ZnSO_4 \cdot 7H_2O$
250 mg/l $CuSO_4 \cdot 5H_2O$
250 mg/l $MnCl_2 \cdot 4H_2O$
50 mg/l $NaMoO_4 \cdot 2H_2O$
835 mg/l $FeCl_3 \cdot 6H_2O$
(**)—vitamins 1000 x:
1 g/l thiamine
1 g/l biotin
1 g/l panthothenate The optimal conditions for growth are at 28° C., pH 7.0.The doubling time is about 2.5 hours.

The usual biochemical methods of purification can be used for the isolation in which the presence of the enzyme in the respective fractions obtained can be easily tested on the basis of the cleavage of its recognition sequence. Lambda DNA is, for example, suitable as the substrate. The DNA fragments obtained are separated electrophoretically in agarose gels in buffer systems usually used for the fragment separation in the presence of ethidium bromide.

The enzyme is isolated and purified by the usual chemical an mechanical methods such as, for example, by high pressure dispersion, ultrasound or enzymatic lysis. The cells are preferably lysed by means of a French press. The further purification of the supernatant is preferably carried out by means of affinity chromatography and ion exchange chromatography. Heparin-Sepharose ® CL-6B (Pharmacia is for example suitable as the material for the affinity chromatography.

The product available under the name DEAE Sephandex ® (Pharmacia) is suitable as the anion-exchanger. Other chromatographic materials which are known to the expert are also suitable.

The following Examples elucidate the invention further.

EXAMPLE 1

*Rhizobium leguminosarum* DSM 5629 is cultured at 28° C. for 32 hours and is harvested in the stationary phase. The culture medium is PSY-medium. The cell paste (30 g wet weight) is resuspended in 2 volumes buffer A (40 mmol/l Tris/HCl, pH 8.0, 0.1 mmol/l EDTA, 7 mmol/l 2-mercaptoethanol), which contains protease inhibitors. Subsequently, the cells are lysed by passing them twice through a French press at 23.000 lb/inch² and the precipitate is separated off. The supernatant is desalted by dialysis against buffer B (40 mmol/l Tris/HCl, pH 8.5, 0.1 mmol/l EDTA, 7 mmol/l 2-mercaptoethanol, 10% (v/v) glycerol) and fractionated on a heparin-Sepharose column which is equilibrated with buffer B. A gradient of 0–1 mol/l NaCl is used for the elution. RleAI is found in the fractions between 0.4 and 0.6 mol/l NaCl. The active fractions are desalted against buffer B on a Sephadex G25 column. Subsequently, they are applied to a Q Sepharose column which was equilibrated with buffer B. A gradient of 0–0.5 mol/l NaCl in buffer B (pH 7.0) is used for the elution. RleAI is found in the fractions between 0.10 and 0.20 mol/l NaCl.

The active fractions are pooled and dialyzed against storage buffer (20 mmol/l Tris-HCl, pH 8.0, 10 mmol/l 2-mercaptoethanol, 100 mmol/l NaCl, 0.1 mmol/l EDTA and 50% (v/v) glycerol).

EXAMPLE 2

Determination of the Activity

Definition of the enzyme units: 1 U RleAI cleaves 1 µg Lambda-DNA within 1 hour at 30° C. in 25 µl final volume.

17.5 µl water and 5 µl lambda DNA (optical density: 4 OD/ml) as well as 1 µl RleAI solution (1 µl ) are added to a mixture of 2.5 µl incubation buffer (100 mmol/l Tris-HCl, pH 7.5/37° C., 100 mmol/l magnesium chloride and 10 mmol/l DTE). The solution is incubated for 1 hour at 30° C., cooled on ice and then 5 µl of a terminating reagent consisting of 7 mmol/l urea, 20% (w/v) sucrose, 60 mmol/l EDTA and 0.01% (w/v) bromophenol blue is added. Subsequently separation is carried out by electrophoresis in 1% agarose gels for 3–4 hours at 100 V. The bands obtained are identified by comparison with a DNA length standard.

We claim:

1. Type II restriction endonuclease capable of recognizing and cleaving the DNA sequence of SEQ ID NO: 1 and cleaving said sequence at the position indicated by the arrows:

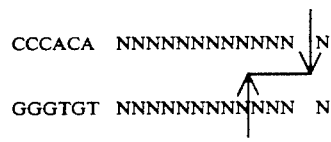

wherein N is A, C, T or G.

2. Restriction endonuclease of claim 1, obtained from microorganisms of the genus Rhizobium.

3. Restriction endonuclease of claim 1, obtained from *Rhizobium leguminosarum* DSM 5629.

4. Restriction endonuclease of claim 1, characterized by a temperature optimum of about 30° C. and a pH optimum of about 7.5 and 8.0.

5. Process for the isolation of a type II restriction endonuclease which recognizes the DNA sequence of SEQ ID NO: 1 and cleaves acid sequence at the position indicated by the arrows:

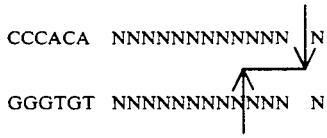

wherein N is A, T, C or G, comprising culturing a microorganism of genus Rhizobium which produces said restriction endonuclease under conditions favoring production of said restriction endonuclease and isolating said restriction endonuclease from said microorganism.

6. Process of claim 2, wherein said microorganism is *Rhizobium leguminosarum* DSM 5629.

7. Process of claim 6, further comprising lysing cells of said microorganism to yield a supernatant and isolating said restriction endonuclease from said supernatant.

8. Process of claim 7, further comprising subjecting said supernatant to affinity chromatography and anion-exchange chromatography to isolate said restriction endonuclease.

9. Process of claim 8, wherein said affinity chromatography is carried out using carrier bound heparin.

10. Method for obtaining a DNA sequence produced by action of the restriction endonuclease of claim 1, comprising contacting a DNA containing sample with said restriction endonuclease and separating cleavage products produced thereby.

* * * * *